US012642492B2

(12) United States Patent
Wang et al.

(10) Patent No.: US 12,642,492 B2
(45) Date of Patent: Jun. 2, 2026

(54) MEDICAL DEVICE AND INFORMATION DISPLAY METHOD THEREFOR

(71) Applicant: SHENZHEN MINDRAY BIO-MEDICAL ELECTRONICS CO., LTD., Shenzhen (CN)

(72) Inventors: Cheng Wang, Shenzhen (CN); Lin Tan, Shenzhen (CN); Xuelei Wu, Shenzhen (CN); Sanchao Liu, Shenzhen (CN); Weiwei Yuan, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 51 days.

(21) Appl. No.: 18/427,800

(22) Filed: Jan. 30, 2024

(65) Prior Publication Data

US 2024/0215930 A1      Jul. 4, 2024

Related U.S. Application Data

(63) Continuation of application No. PCT/CN2022/109507, filed on Aug. 1, 2022.

(30) Foreign Application Priority Data

Jul. 30, 2021      (CN) .......................... 202110872597.9

(51) Int. Cl.
*G08B 23/00*      (2006.01)
*A61B 5/00*      (2006.01)
(Continued)

(52) U.S. Cl.
CPC ............ *A61B 5/743* (2013.01); *A61B 5/7435* (2013.01); *A61B 5/746* (2013.01); *G16H 10/60* (2018.01); *G16H 40/63* (2018.01)

(58) Field of Classification Search
CPC ....... A61B 5/743; A61B 5/7435; A61B 5/746; A61B 5/0205; A61B 5/024; A61B 5/031;
(Continued)

(56) References Cited

U.S. PATENT DOCUMENTS 7,945,452 B2 *    5/2011  Fathallah ................ G16Z 99/00
                                                                705/2
8,863,031 B2 *   10/2014  Douen ................... G16H 40/67
                                                                715/705

(Continued)

FOREIGN PATENT DOCUMENTS

CN        108474830 A        8/2018
CN        111212599 A        5/2020
CN        111493885 A        8/2020

OTHER PUBLICATIONS

International Search Report issued in corresponding International Application No. PCT/CN2022/109507, mailed Oct. 26, 2022, 4 pages.

(Continued)

*Primary Examiner* — Toan N Pham
(74) *Attorney, Agent, or Firm* — Morgan, Lewis & Bockius LLP

(57) ABSTRACT

A medical device and an information display method are disclosed. The medical device includes a memory for storing an executable program, a processor and a display. The processor is used for executing the executable program to perform following operations: acquiring patient data of a patient, which includes monitoring data of one or more vital sign parameters of the patient; analyzing the patient data according to preset rules to obtain the patient state of the patient and a comparison result of at least one vital sign parameter associated with the patient state and a preset alarm condition; and presenting in the display the patient state on a human body diagram, and via text or graphics, the (Continued)

100 comparison result of the at least one vital sign parameter associated with the patient state and the preset alarm condition.

19 Claims, 6 Drawing Sheets

(51) Int. Cl.
*G16H 10/60* (2018.01)
*G16H 40/63* (2018.01)

(58) Field of Classification Search
CPC .... A61B 5/14542; A61B 5/363; G16H 10/60; G16H 40/63
See application file for complete search history.

(56) References Cited

U.S. PATENT DOCUMENTS 8,956,292 B2 * 2/2015 Wekell ................ G06F 3/04842
600/301

9,161,696 B2 * 10/2015 Al-Ali ..................... A61B 5/742
9,211,096 B2 * 12/2015 Tremper .............. A61B 5/4821
9,265,429 B2 * 2/2016 St. Pierre ............. A61B 5/7475
9,943,269 B2 * 4/2018 Muhsin .............. A61B 5/14551
2007/0050715 A1 3/2007 Behar
2009/0024008 A1 1/2009 Brunner et al.
2015/0097701 A1 4/2015 Al-Ali et al.
2015/0164437 A1 * 6/2015 McCombie ........... A61B 5/1117
600/301
2019/0117070 A1 4/2019 Muhsin et al.

OTHER PUBLICATIONS

Extended European Search Report issued in related European Application No. 22848719.5, mailed Oct. 8, 2024, 10 pages.
Shenzhen Mindray Bio-Medical Electronics Co., Ltd., European Office Action, EP Patent Application No. 22848719.5, Jun. 26, 2025, 6 pgs.
Shenzhen Mindray Bio-Medical Electronics Co., Ltd., European Office Action, EP Patent Application No. 22848719.5, Apr. 9, 2026, 7 pgs.

* cited by examiner

100

900

Figures 10, 11:
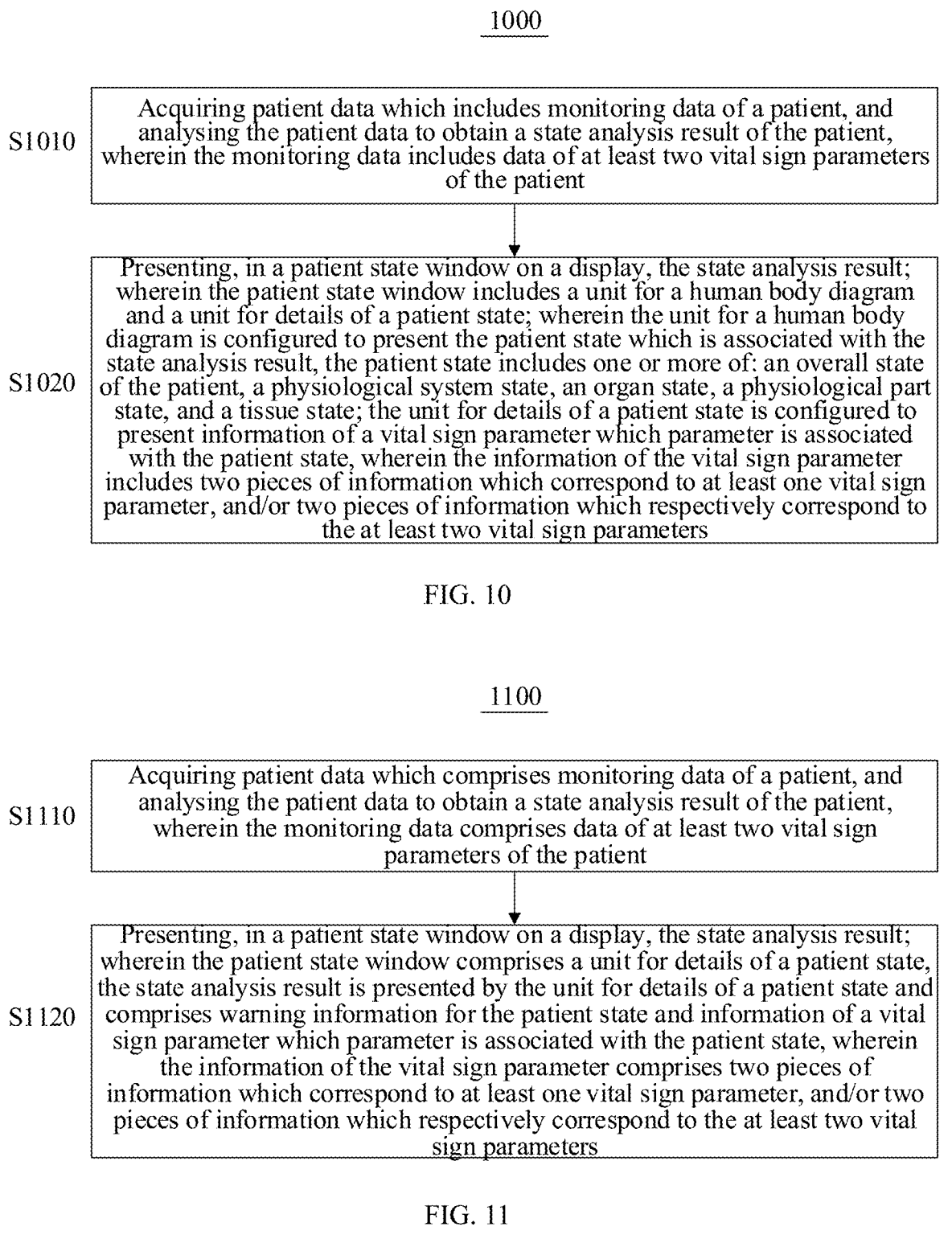

1000

| | Acquiring patient data which includes monitoring data of a patient, and analysing the patient data to obtain a state analysis result of the patient, wherein the monitoring data includes data of at least two vital sign parameters of the patient |
|---|---|
| S1010 | |

| | Presenting, in a patient state window on a display, the state analysis result; wherein the patient state window includes a unit for a human body diagram and a unit for details of a patient state; wherein the unit for a human body diagram is configured to present the patient state which is associated with the state analysis result, the patient state includes one or more of: an overall state of the patient, a physiological system state, an organ state, a physiological part state, and a tissue state; the unit for details of a patient state is configured to present information of a vital sign parameter which parameter is associated with the patient state, wherein the information of the vital sign parameter includes two pieces of information which correspond to at least one vital sign parameter, and/or two pieces of information which respectively correspond to the at least two vital sign parameters |
|---|---|
| S1020 | |

| | Acquiring patient data which comprises monitoring data of a patient, and analysing the patient data to obtain a state analysis result of the patient, wherein the monitoring data comprises data of at least two vital sign parameters of the patient |
|---|---|
| S1110 | |

| | Presenting, in a patient state window on a display, the state analysis result; wherein the patient state window comprises a unit for details of a patient state, the state analysis result is presented by the unit for details of a patient state and comprises warning information for the patient state and information of a vital sign parameter which parameter is associated with the patient state, wherein the information of the vital sign parameter comprises two pieces of information which correspond to at least one vital sign parameter, and/or two pieces of information which respectively correspond to the at least two vital sign parameters |
|---|---|
| S1120 | |

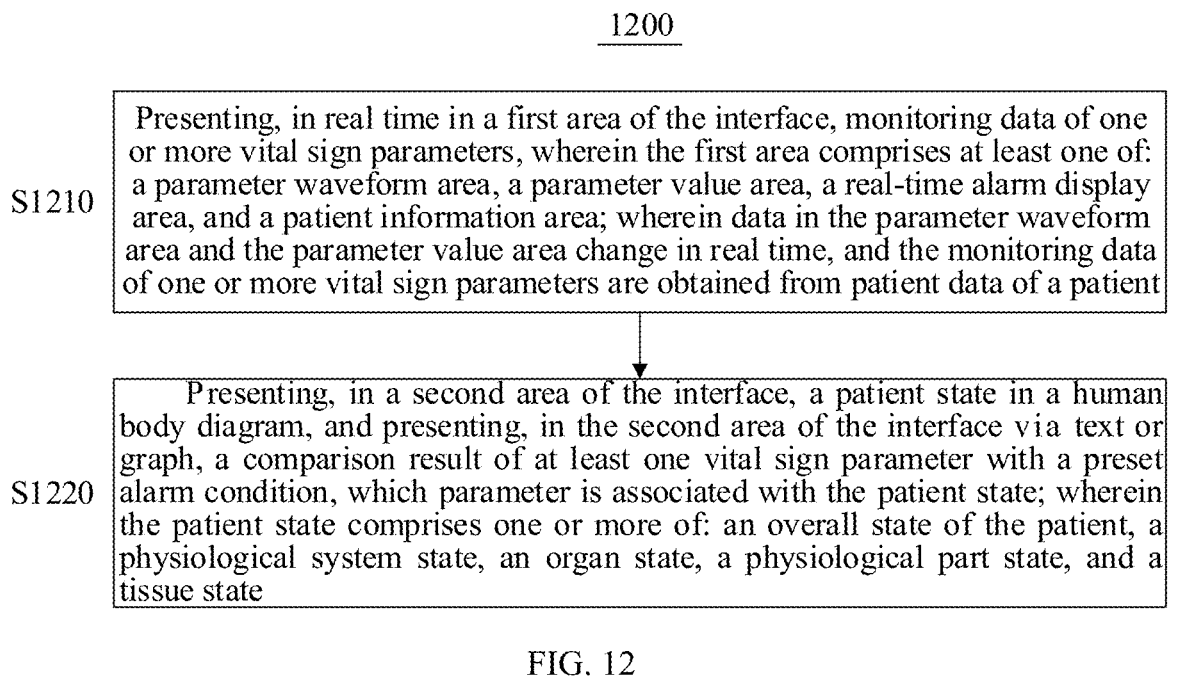

| | |
|---|---|
| S1210 | Presenting, in real time in a first area of the interface, monitoring data of one or more vital sign parameters, wherein the first area comprises at least one of: a parameter waveform area, a parameter value area, a real-time alarm display area, and a patient information area; wherein data in the parameter waveform area and the parameter value area change in real time, and the monitoring data of one or more vital sign parameters are obtained from patient data of a patient |
| S1220 | Presenting, in a second area of the interface, a patient state in a human body diagram, and presenting, in the second area of the interface via text or graph, a comparison result of at least one vital sign parameter with a preset alarm condition, which parameter is associated with the patient state; wherein the patient state comprises one or more of: an overall state of the patient, a physiological system state, an organ state, a physiological part state, and a tissue state |

FIG. 12

MEDICAL DEVICE AND INFORMATION DISPLAY METHOD THEREFOR

CROSS-REFERENCE

This application is a continuation International Application No. PCT/CN2022/109507, filed Aug. 1, 2022, which claims benefit of priority to Chinese Application No. 202110872597.9, filed Jul. 30, 2021. The contents of all the above application are incorporated herein by reference.

TECHNICAL FIELD

The disclosure relates to a technical field for a medical device, and more particularly to a medical device and an information display method therefor.

BACKGROUND

At present, after a medical device, such as a monitor, acquires patient data, the medical device usually directly displays, on its display screen, the patient data, such as waveform data, parameter value data, etc. In addition, some alarm data are also displayed. Medical staff need to determine a current state of the patient by themselves based on various data on the display screen, and cannot see the state of the patient intuitively and clearly at a glance.

SUMMARY

This disclosure is proposed so as to solve the above-mentioned problem. According to an aspect of this disclosure, a medical device is provided, which includes a memory, a processor, and a display; wherein the memory is configured to store an executable program; the processor is configured to execute the executable program, so as to enable the processor to implement following operations: acquiring patient data of a patient, wherein the patient data at least includes monitoring data of one or more vital sign parameters of the patient; analysing the patient data according to a preset rule, so as to obtain a patient state of the patient and a comparison result of at least one vital sign parameter with a preset alarm condition, which parameter is associated with the patient state; wherein the patient state includes one or more of an overall state of the patient, a physiological system state, an organ state, a physiological part state, and a tissue state; and presenting, on a human body diagram on the display, the patient state, and presenting, via text or graph on the display, the comparison result of the at least one vital sign parameter with the preset alarm condition, which parameter is associated with the patient state.

According to another aspect of this disclosure, a medical device is provided, which includes a memory, a processor, and a display; wherein the memory is configured to store an executable program; the processor is configured to execute the executable program, so as to enable the processor to implement following operations: acquiring patient data which includes monitoring data of a patient, and analysing the patient data to obtain a state analysis result of the patient, wherein the monitoring data includes data of at least two vital sign parameters of the patient; presenting, in a patient state window on the display, the state analysis result, wherein the patient state window includes a unit for details of a patient state, wherein the state analysis result is presented by the unit for details of a patient state and includes warning information for the patient state and information of a vital sign parameter, which parameter is associated with the patient state, wherein the information of the vital sign parameter includes two pieces of information which correspond to at least one vital sign parameter, and/or two pieces of information which respectively correspond to the at least two vital sign parameters.

According to yet another aspect of this disclosure, an information display method for a medical device is provided, which includes: acquiring patient data which includes monitoring data of a patient, and analysing the patient data to obtain a state analysis result of the patient, wherein the monitoring data includes data of at least two vital sign parameters of the patient; and presenting, in a patient state window on a display, the state analysis result; wherein the patient state window includes a unit for a human body diagram and a unit for details of a patient state; wherein the unit for a human body diagram is configured to present the patient state which is associated with the state analysis result, the patient state includes one or more of an overall state of the patient, a physiological system state, an organ state, a physiological part state, and a tissue state; the unit for details of a patient state is configured to present information of a vital sign parameter, which parameter is associated with the patient state, wherein the information of the vital sign parameter includes two pieces of information which correspond to at least one vital sign parameter, and/or two pieces of information which respectively correspond to the at least two vital sign parameters.

According to further another aspect of this disclosure, an information display method for a medical device is provided, which includes: acquiring patient data which includes monitoring data of a patient, and analysing the patient data to obtain a state analysis result of the patient, wherein the monitoring data includes data of at least two vital sign parameters of the patient; and presenting, in a patient state window on a display, the state analysis result; wherein the patient state window includes a unit for details of a patient state; wherein the unit for details of a patient state is configured to present the state analysis result, which includes warning information for the patient state and information of a vital sign parameter, which parameter is associated with the patient state, wherein the information of the vital sign parameter includes two pieces of information which correspond to at least one vital sign parameter, and/or two pieces of information which respectively correspond to the at least two vital sign parameters.

According to further another aspect of this disclosure, a display method for an interface of a monitoring device is provided, including: presenting, in real time in a first area of the interface, monitoring data of one or more vital sign parameters, wherein the first area includes at least one of a parameter waveform area, a parameter value area, a real-time alarm display area, and a patient information area, wherein data in the parameter waveform area and the parameter value area change in real time, and the monitoring data of one or more vital sign parameters are obtained from patient data of a patient; presenting, on a human body diagram in a second area of the interface, a patient state of the patient, and presenting, via text or graph in the second area of the interface, a comparison result of the at least one vital sign parameter with a preset alarm condition, which parameter is associated with the patient state; wherein the patient state includes one or more of an overall state of the patient, a physiological system state, an organ state, a physiological part state, and a tissue state.

According to the medical device and information display method therefore according to the embodiment of this disclosure, patient data is analysed to obtain a patient state analysis result, and the patient state is graphically presented to the medical staff, and the parameters are detailly presented to the medical staff, so that the medical staff can intuitively and clearly know the patient state, making it easier for medical staff to quickly take treatment measure according to the patient state.

BRIEF DESCRIPTION OF THE DRAWINGS

The above and other objects, features and advantages of this disclosure become more apparent through a more detailed description of embodiments of this disclosure in conjunction with the accompanying drawings. The drawings are used to provide further understanding of the embodiments of this disclosure, and constitute a part of the specification, and used to explain this disclosure together with the embodiments of this disclosure, and do not constitute a limitation of this disclosure. In the drawings, similar reference numbers generally represent similar components or steps.

FIG. 10 is a flowchart diagram of an information display method for a medical device according to an embodiment of this disclosure.

FIG. 11 is a flowchart diagram of information display method for a medical device according to another embodiment of this disclosure.

FIG. 12 is a flowchart diagram of information display method for a medical device according to another further embodiment of this disclosure.

DETAILED DESCRIPTION

In order to make the purpose, technical solution, and advantages of this disclosure more obvious, the following refers to the attached drawings to describe in detail the exemplary embodiments according to this disclosure. Obviously, the described embodiments are only some of the embodiments of this disclosure, not all of them. It should be understood that this disclosure is not limited by the embodiments described here. Based on the embodiments described in this disclosure, all other embodiments acquired by those skilled in the art without creative work, fall within the protection scope of this disclosure.

Figure 1:
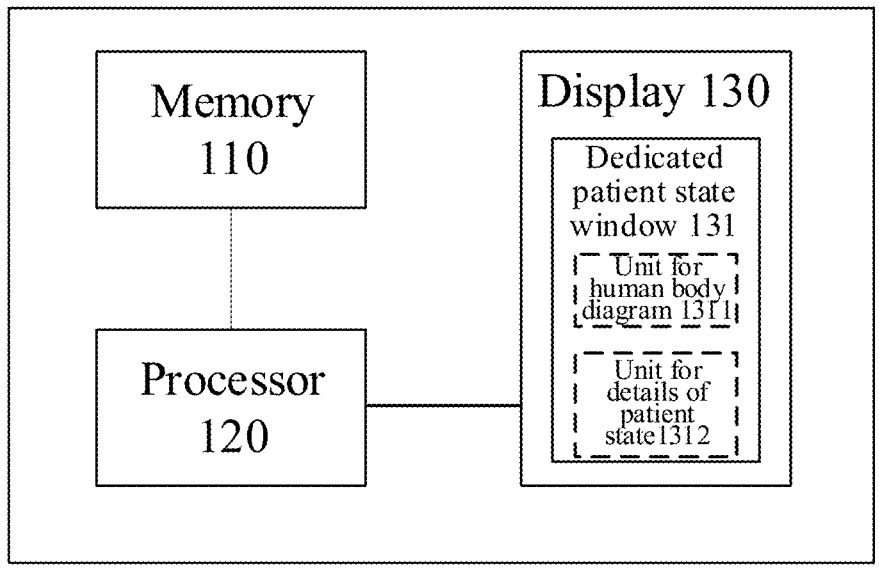
FIG. 1 is a block diagram of a medical device according to an embodiment of this disclosure.

Firstly, a medical device according to an embodiment of this disclosure is described with reference to FIG. 1. FIG. 1 is a block diagram of a medical device 100 according to an embodiment of this disclosure. As shown in FIG. 1, the medical device 100 includes a memory 110, a processor 120 and a display 130; wherein the memory 110 is configured to store an executable program; the processor 120 is configured to execute the executable program, so as to enable the processor 120 to implement following operations: acquiring patient data of a patient, which data at least includes monitoring data of one or more vital sign parameters of the patient; analysing the patient data according to a preset rule, so as to obtain a patient state of the patient and a comparison result of at least one vital sign parameter with a preset alarm condition, which parameter is associated with the patient state; wherein the patient state includes one or more of an overall state of the patient, a physiological system state, an organ state, a physiological part state, and a tissue state; and presenting, on a human body diagram on the display 130, the patient state, and presenting, via text or graph on the display 130, the comparison result of the at least one vital sign parameter with the preset alarm condition, which parameter is associated with the patient state.

In an embodiment of this disclosure, after the medical device 100 obtains the patient data (including at least monitoring data, and may also including treatment device data, drug administration data, laboratory test data, imaging data, diagnostic data, etc.), the medical device 100 analyses the patient data according to a preset rule, so as to obtain a patient state of the patient and a comparison result of at least one vital sign parameter with a preset alarm condition, which parameter is associated with the patient state. For example, the medical device 100 analyses the patient data based on a state determination rule database stored in the memory 110. The state determination rule database stores rules for determining the patient state. These rules can be preset by the user, or can be automatically generated through big data learning. The automatically generated rules can be processed manually to eventually form recognized rules in the rule base. Then, on the display 130, the patient state is presented on a human body diagram, and the comparison result of at least one vital sign parameter with a preset alarm condition, which parameter is associated with the patient state, is presented via text or graph. For example, a dedicated patient state window 131 may be configured to display the patient state and the comparison result of at least one vital sign parameter with a preset alarm condition, which parameter is associated with the patient state. Here, the "dedicated patient state window" can be understood as a window that is different and independent from common areas or windows that display patient data, alarm data, etc., on a medical device, such as a monitor. Specifically, the patient state window 131 includes a unit for a human body diagram 1311 and a unit for details of a patient state 1312, wherein the unit for a human body diagram 1311 displays the patient state, such as one or more of an overall state of the patient, a physiological system state, an organ state, a physiological part state, and a tissue state. The unit for details of a patient state 1312 displays the comparison result of the at least one vital sign parameter with the preset alarm condition, which parameter is associated with the patient state, such as an alarm which is generated when at least one vital sign parameter, which is associated with the patient state, satisfies a preset alarm condition, and a duration of the alarm, etc. In an embodiment of this disclosure, the patient data is analysed, so as to obtain the patient state and the comparison result of at least one vital sign parameter with a preset alarm condition, which parameter is associated with the patient state, and the patient state is graphically presented to the medical staff on a human body diagram, while the comparison result of at least one vital sign parameter with a preset alarm condition, which parameter is associated with the patient state, is further presented to the medical staff via text or graph, so that the medical staff can intuitively and clearly know the patient state and related alarm condition, thereby facilitating the medical staff to quickly take treatment measure according to the patient state.

In an embodiment of this disclosure, the unit for a human body diagram 1311 can present a human body diagram, and present the patient state by marking the human body diagram. On the human body diagram, when the patient state includes the overall state of the patient, the entirety human body diagram is marked. When the patient state includes one or more of the physiological system state, the organ state, the physiological part state, and the tissue state, one or more of physiological system, organ, physiological part, and tissue, which corresponds/correspond to the patient state, are marked. Therefore, the human body diagram may be a complete human body diagram (including a complete human body) or at least a partial human body diagram (including at least a partial human body). By presenting the human body diagram and marking the human body diagram to present the patient state, medical staff can very intuitively view the overall state of the patient or the state of certain physiological system, organ, physiological part, tissue, etc., of the patient.

In an embodiment of this disclosure, the human body diagram can be marked via at least one of graph information, symbol information, color information, and text information, which is located on or adjacent to the human body diagram, thereby presenting the patient state. The patient state may include whether one or more of the overall state of the patient, physiological system state, organ state, physiological part state and tissue state is/are abnormal or not, and one or more of an abnormality level, a criticality level, and a nursing level. An exemplary description is given below in conjunction with FIG. 2.

Figure 2:
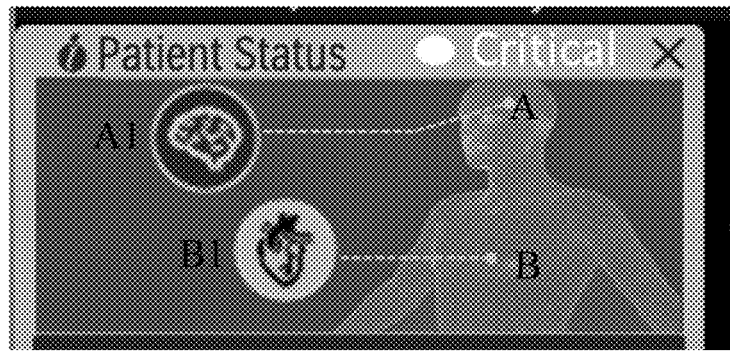
FIG. 2 is a diagram of an example of a unit for a human body diagram in a patient state window displayed by a medical device according to an embodiment of this disclosure.

FIG. 2 is a diagram of an example of a unit for a human body diagram in a patient state window displayed by a medical device according to an embodiment of this disclosure. As shown in FIG. 2, in this example, the unit for a human body diagram displays the human body diagram including an upper body and a head, in which relevant physiological parts A and B (brain and heart, respectively) are marked on the human body diagram, indicating that states of the physiological parts A and B have been analysed based on the acquired patient data. Usually, these states are abnormal, because marking the abnormal state is more meaningful. However, these states may also be normal, which depends on whether the patient state window is permanently displayed or is just displayed when abnormal. This is to be described later.

In addition, state information A1 and B1 of the physiological parts A and B are displayed adjacent to the human body diagram (peripheral area). In the example shown in FIG. 2, the state information A1 and B1 include a drawn structure of the physiological part (the brain and the heart, respectively) and the state of the physiological part which is presented in color information. Here, since it is a grayscale image, the display effect is not obvious. In practical applications, for example, red lines, red fills, etc., can be configured to present abnormalities of the physiological parts, and a shade of red color can also be configured to present abnormality levels. In this example, the human body diagram is marked with graph information and color information to present the patient state. The patient state is presented in the peripheral area of the human body diagram. In addition, whether the physiological part of the patient is abnormal, and the abnormality level of the physiological part are presented. In other examples, the state of a certain physiological part of the patient can also be presented via other ways and other locations, such as via symbolic information and/or text information. The location of presentation may not be the peripheral area of the human body diagram, but at the human body diagram. In addition, other state of a certain physiological part can also be presented, such as criticality level and/or nursing level, etc. Furthermore, in the example of FIG. 2, the state of a specific physiological part of the patient is shown. But this is only exemplary, and the overall state of the patient may also be shown, such as the criticality level and/or nursing level of the patient, etc. Similarly, the overall state of the patient can also be presented via at least one of symbol information, color information, and text information. In this case, the human body diagram may be the entirety human body, or the human body diagram may not be included. For example, when the patient is normal, text "Normal" is displayed in a green background, when the patient is critical, text "Critical" is displayed in a red background. Similarly, the physiological system state, organ state, tissue state of the patient, etc., can also be presented in a similar manner as described above.

In an embodiment of this disclosure, the comparison result of at least one vital sign parameter with a preset alarm condition, which parameter is associated with the patient state, which result is presented by the unit for details of a patient state 1312, may include an alarm which is generated when at least one vital sign parameter, which is associated with the patient state, satisfies a preset alarm condition, and a duration of the alarm, etc. In addition, it can also be other time information of the alarm, such as interval time of the alarm, occurrence frequency within unit time, etc. Among them, the preset alarm condition may include a preset alarm condition for exceeding a limit (for example, a certain parameter value exceeds its preset threshold) or a preset alarm condition for an abnormal event (for example, an abnormal event occurs). Presenting, via text, the comparison result of the at least one vital sign parameter with the preset alarm condition, which parameter is associated with the patient state, may include combining an alarm for exceeding a limit of and/or an alarm for an abnormal event of the at least one vital sign parameter, which parameter is associated with the patient state, with duration(s) of the alarm for exceeding a limit and/or the alarm for an abnormal event; and presenting the alarm for exceeding a limit and/or the alarm for an abnormal event and the duration(s) of the alarm for exceeding a limit and/or the alarm for an abnormal event. That is to say, the alarm and time information can be presented in a combined manner, so that they jointly reflect one or more of the overall state of the patient, the same physiological system state, the same organ state, the same physiological part state, and the same tissue state. Herein, the alarm and time information can be presented in a combined manner, can be understood as using hyphens (such as commas, semicolons, etc.), connecting words (such as "and", "also", "accompanied by", etc.) to combine and present the alarm and alarm-related time information, so as to form combined alarm information. Compared with non-combined alarm information that does not include time information, the combined alarm information can present more specific alarm information to medical staff in multiple dimensions. So that medical staff can have a clearer understanding of the patient condition. The comparison result of the vital sign parameter with the preset alarm condition can be displayed on the display 130 when the duration of the alarm exceeds a preset time period. In this way, the presentation of alarm information, that temporarily satisfies the alarm condition and then recovers on its own can, be ignored, allowing medical staff to only focus on long-term alarm information that requires more attention.

In another embodiment, the patient data includes monitoring data of a first vital sign parameter and monitoring data of a second vital sign parameter, and the preset alarm condition requires to simultaneously satisfy conditions for occurrence of a first alarm for exceeding a limit and/or a first alarm for an abnormal event, and for occurrence of a second alarm for exceeding a limit and/or a second alarm for an abnormal event. Presenting, via text, the comparison result of the at least one vital sign parameter with the preset alarm condition, which parameter is associated with the patient state, includes combing and presenting followings: a first alarm for exceeding a limit and/or a first alarm for an abnormal event of a first vital sign parameter, which parameter is associated with the patient state; and a second alarm for exceeding a limit and/or a second alarm for an abnormal event of a second vital sign parameter, which parameter is associated with the patient state; wherein the first alarm for exceeding a limit and/or the first alarm for an abnormal event, and the second alarm for exceeding a limit and/or the second alarm for an abnormal event, simultaneously occur. In this embodiment, the unit for details of a patient state 1312 presents two alarms which respectively correspond to two vital sign parameters, wherein the two alarms are presented in a combined manner and jointly reflect one or more of the overall state of the patient, the same physiological system state, the same organ state, the same physiological part state, and the same tissue state. Here, two alarms are presented as a group, which is also a kind of combined alarm information, and can present related alarm information to medical staff, so that medical staff can understand the patient condition more clearly.

Furthermore, the aforementioned presenting, via text, the comparison result of the at least one vital sign parameter with the preset alarm condition, which parameter is associated with the patient state, includes combing and presenting followings: a first alarm for exceeding a limit and/or a first alarm for an abnormal event of a first vital sign parameter, which parameter is associated with the patient state; a second alarm for exceeding a limit and/or a second alarm for an abnormal event of a second vital sign parameter, which parameter is associated with the patient state; and a duration in which: the first alarm for exceeding a limit and/or the first alarm for an abnormal event, and the second alarm for exceeding a limit and/or the second alarm for an abnormal event, simultaneously occur. In this embodiment, the unit for details of a patient state 1312 presents two alarms which respectively correspond to two vital sign parameters and the durations of the two alarms, which jointly reflect one or more of the overall state of the patient, the same physiological system state, the same organ state, the same physiological part state, and the same tissue state. Here, two alarms and the durations thereof are presented as a group, which is also a kind of combined alarm information, and can present related alarm information to medical staff, so that medical staff can understand the patient condition more clearly. An exemplary description is given below in conjunction with FIG. 3.

Figure 3:
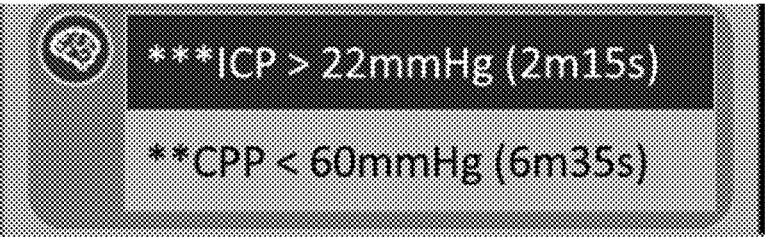
FIG. 3 is a diagram of an example of a unit for details of a patient state of a patient state window displayed by a medical device according to an embodiment of this disclosure.

FIG. 3 is a diagram of an example of a unit for details of a patient state of a patient state window displayed by a medical device according to an embodiment of this disclosure. As shown in FIG. 3, in this embodiment, the unit for details of a patient state shows information of two vital sign parameters, including information of intracranial pressure (ICP) and information of cerebral perfusion pressure (CPP). The ICP information includes two kinds of information, namely alarm and time information related to the alarm— ICP has been greater than 22 mmHg for 2 minutes and 15 seconds. The CPP information includes two kinds of information, namely alarm and time information related to the alarm—CPP has been below 60 mmHg for 6 minutes and 35 seconds. These information of two vital sign parameters are related to an abnormal state of brain of the patient. That is, FIG. 3 is the information of the vital sign parameter which is associated to an abnormal physiological part shown in FIG. 2. Since it is the information of the vital sign parameter for the abnormal state, therefore it can also be regarded as alarm information. In the example shown in FIG. 3, the unit for details of a patient state uses text information to present two alarms corresponding to two vital sign parameters and the time information of each alarm, wherein the time information expresses that the information of the vital sign parameter exceeds its safety threshold for a time period (i.e. the duration of the alarm). In other examples, the unit for details of a patient state can also combine sound, light, and other indication information to further remind the current alarm information.

Furthermore, in other examples, the comparison result of the at least one vital sign parameter with the preset alarm condition, which parameter is associated with the patient state, can be presented via graph. For example, the comparison result of the at least one vital sign parameter with the preset alarm condition, which parameter is associated with the patient state, can be presented via a curve graph, a histogram, a bar graph, a box graph, a scatter graph, a broken line graph, or a combination thereof, so that medical staff can more intuitively understand changes in the vital sign parameter itself and/or changes in the comparison result of the vital sign parameter with the preset alarm condition.

In a further embodiment of this disclosure, the processor 120 may also control the display 130 to present patient deterioration warning information and/or treatment suggestion information which are/is generated according to the patient state. For example, this information may be displayed in the patient state window 131. The processor 120 can predict a possible future situation of the patient based on the previously obtained state analysis result, thereby generating patient deterioration warning information (text indication information such as "possible shock" or other indicative information). The patient deterioration warning information may be displayed in the unit for details of a patient state 1312, may also be displayed in the unit for a human body diagram 1311, or may be displayed in other display areas within the patient state window 131. In addition, the processor 120 can also generate treatment suggestion information (text indication information such as "suggest oxygen inhalation" or other indicative information) based on the previously obtained state analysis result. The treatment suggestion information can be displayed in the unit for details of a patient state 1312, can also be displayed in the unit for a human body diagram 1311, and can also be displayed in other display areas in the patient state window 131.

In an embodiment of this disclosure, when the unit for a human body diagram 1311 presents multiple physiological system states, multiple organ states, multiple physiological part states, or multiple tissue states, the unit for details of a patient state 1312 is configured to present the information of vital sign parameter in multiple groups. Information of each group of vital sign parameter is associated with one physiological system state, one organ state, one physiological part state, or one tissues state. In this way, information of vital sign parameter, which parameter is associated with the state of each physiological system, organ, physiological part, and tissue, can be more clearly presented. An exemplary description is given below in conjunction with FIG. 4.

Figure 4:
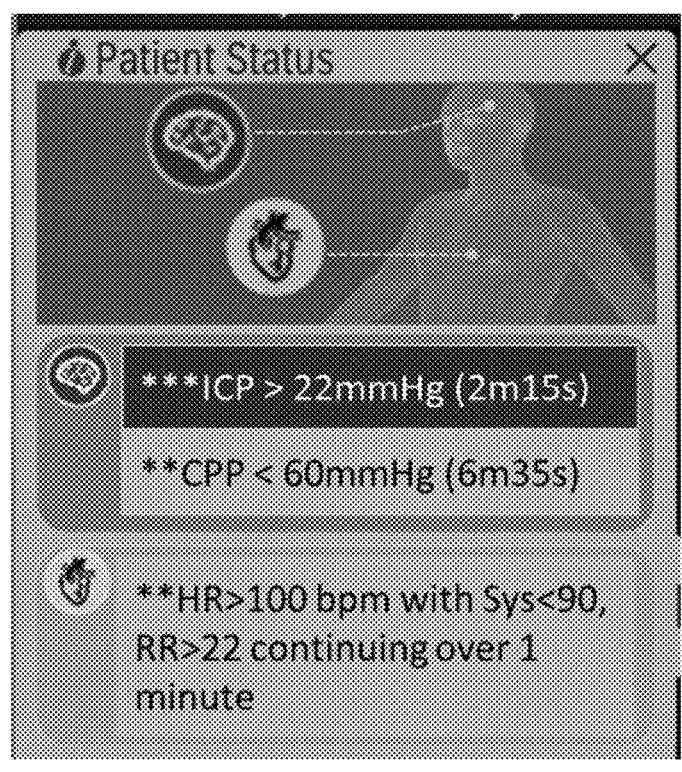
FIG. 4 is a diagram of an example of a patient state window displayed by a medical device according to an embodiment of this disclosure.

FIG. 4 is a diagram of an example of a patient state window displayed by a medical device according to an embodiment of this disclosure. As shown in FIG. 4, in this example, the patient state window includes a unit for a human body diagram and a unit for details of a patient state. The unit for a human body diagram displays the human body diagram including the upper body and head, in which two related physiological parts—the brain and the heart—are marked on the human body diagram. In addition, the state information of these two physiological parts is displayed in a left area of the human body diagram, including a drawn structure of the physiological part and the state of the part presented in color information. Here, since it is a grayscale image, the display effect is not obvious. In practical applications, for example, red lines, red fills, etc., can be configured to present abnormalities of the physiological parts, and a shade of red color can also be configured to present abnormality levels. In other examples, the states of the physiological parts of the patient may be presented in other ways.

Continuing to refer to FIG. 4, the unit for details of a patient state shows the information of the vital sign parameter. Since the unit for a human body diagram displays two physiological parts, the information of the vital sign parameter here includes two groups of information, which groups are respectively associated with two physiological parts. A first group of information of vital sign parameter includes intracranial pressure (ICP) has been greater than 22 mmHg for 2 minutes and 15 seconds, and cerebral perfusion pressure (CPP) has been lower than 60 mmHg for 6 minutes and 35 seconds. These information of the two vital sign parameters are related to an abnormal state of brain of the patient. A second group of information of vital sign parameter includes a sustained heart rate (HR) is greater than 100 and accompanied by a systolic blood pressure which is less than 90 mmHg and a respiratory rate which is greater than 22 per minute. This parameter information is related to an abnormal state of heart of the patient.

In an embodiment of this disclosure, the processor 120 may also control the display 130 to present a trend graph of at least one vital sign parameter in a preset time period, where the trend graph is configured to reflect an evolution situation of the at least one vital sign parameter in the preset time period. For example, the patient state window 131 further includes a display unit for a change of physical sign (not shown in FIG. 1) that presents a trend graph in a preset time period for at least one vital sign parameter (such as the vital sign parameter presented in the unit for details of a patient state 1312 or other vital sign parameters). This trend graph is configured to reflect an evolution situation of the vital sign parameter in the preset time period, which allows medical staff to have a more detailed understanding of the evolution situation of the vital sign parameter, which is associated with the current patient state. The trend graph of the vital sign parameter may include a trend graph of a parameter value of the vital sign parameter (for example, a heart rate value), or may include trend graphs of some abnormal events, which correspond to the vital sign parameter (for example, an arrhythmia event corresponding to the electrocardiogram parameter, such as atrial fibrillation, ventricular fibrillation, etc.) An exemplary description is given below in conjunction with FIG. 5.

Figure 5:
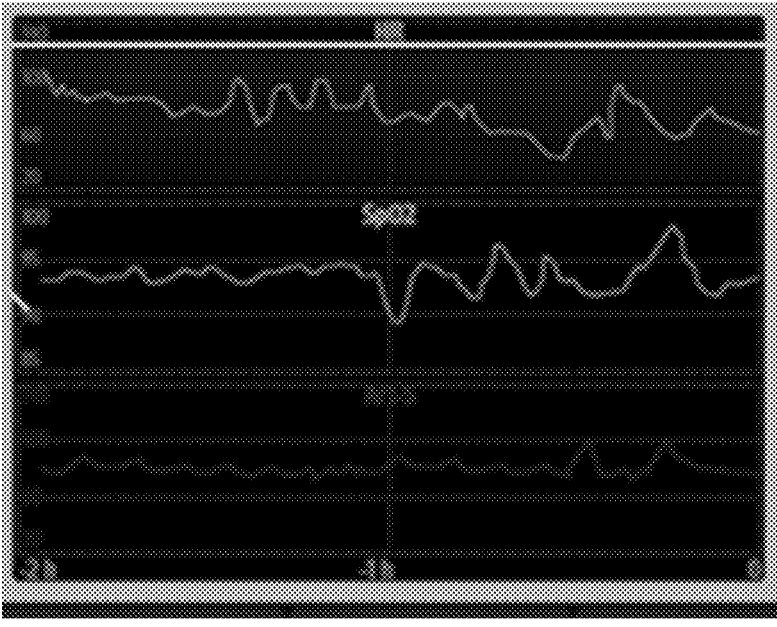
FIG. 5 is a diagram of an example of a display unit for a change of physical sign in a patient state window displayed by a medical device according to an embodiment of this disclosure.

FIG. 5 is a diagram of an example of a display unit for a change of physical sign in a patient state window displayed by a medical device according to an embodiment of this disclosure. As shown in FIG. 5, the display unit for a change of physical sign displays a fluctuation of a vital sign value within a preset time period, which can help medical staff understand the trend and detail of the change of the patient state. In the example shown in FIG. 5, the display unit for a change of physical sign displays the fluctuation of HR and the waveform of blood oxygen saturation (SpO2), which are related to the information of the vital sign parameter displayed in the unit for details of a patient state shown in FIG. 3.

In an embodiment of this disclosure, the processor 120 may also control the display 130 to present personalized concern information of the patient, which is generated according to the patient state. For example, the personalized concern information of the patient, such as a nursing concern, a treatment concern, a safety concern, etc., or such as a pain state, a pupil change, patient consciousness, infection risk of the patient, etc., can be presented in the patient state window, such as in the display unit for a change of physical sign, or other locations. An exemplary description is given below in conjunction with FIG. 6.

Figure 6:
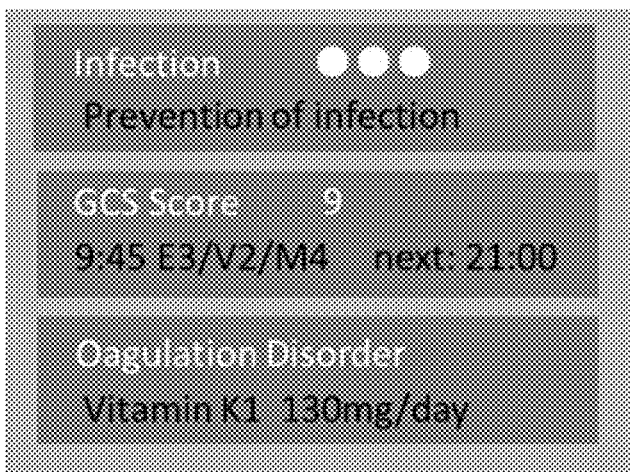
FIG. 6 is a diagram of another example of a display unit for a change of physical sign in a patient state window displayed by a medical device according to an embodiment of this disclosure.

FIG. 6 is a diagram of another example of a display unit for a change of physical sign in a patient state window displayed by a medical device according to an embodiment of this disclosure. As shown in FIG. 6, the display unit for a change of physical sign displays some personalized concern information of the patient, including infection, consciousness in nervous system (GCS Score), nutrition, coagulation disorder and other key concern information. Each concern information includes a concern type, a concern situation, a treatment measure and/or a follow-up suggestion. Taking infection as an example, the concern type is "infection"; the concern situation is an infection severity level (as shown in FIG. 6 with three white circles, a number of circles represents a severity level, herein three circles represent susceptibility to infection, this is only exemplary); the treatment measure and/or follow-up recommendation is/are "Prevention of infection". It can be seen from the example shown in FIG. 6 that, presenting the personalized concern information of the patient by the display unit for a change of physical sign can present more detailed patient state and risk indication to medical staff, making it easier for medical staff to manage.

Figure 7:
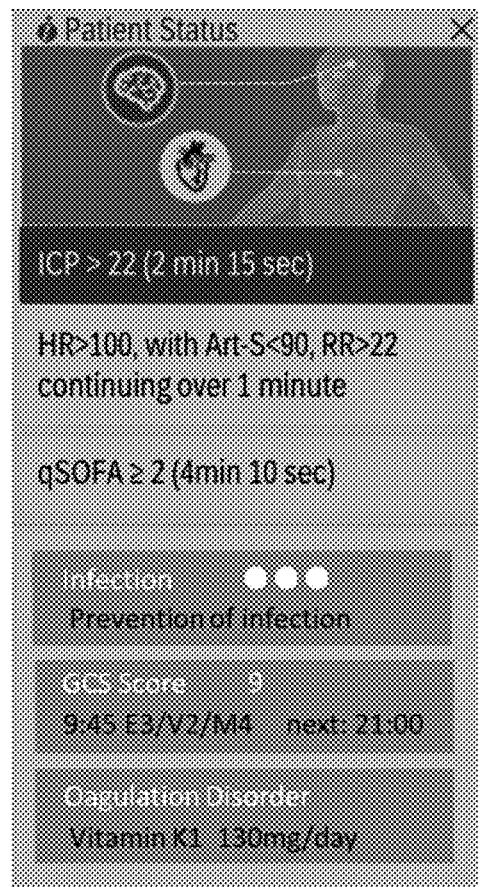
FIG. 7 is a diagram of another example of a patient state window displayed by a medical device according to an embodiment of this disclosure.

FIG. 7 is a diagram of another example of a patient state window displayed by a medical device according to an embodiment of this disclosure. As shown in FIG. 7, the patient state window may include a unit for a human body diagram, a unit for details of a patient state, and a display unit for a change of physical sign. Wherein, the unit for a human body diagram shows a human body diagram in which two relevant physiological parts—the brain and the heart part—are marked on the human body diagram. In addition, the state information of these two physiological parts is displayed in a left area of the human body diagram, including a drawn structure of the physiological part and the state of the physiological part presented in color information. The unit for details of a patient state shows the information of the vital sign parameter. Since the unit for a human body diagram displays two physiological parts, the information of the vital sign parameters here includes two groups of information, which groups are respectively associated with two physiological parts. The display unit for a change of physical sign shows some personalized concern information of the patient. Based on such patient state window, the medical device of this disclosure can intuitively present the patient state, the relevant vital sign parameter which reflects the patient state, and the personalized concern information of the patient to the medical staff, so that the medical staff can know the patient state and risk indication at a glance, so as to facilitate the medical staff to quickly take treatment measure according to the patient state.

In an embodiment of this disclosure, the medical device 100 may be a monitor, a central station, a mobile terminal, and other devices. Generally, the medical device 100 also needs to display some direct patient data on the display 130, such as waveform data, parameter value data, and some alarm information. Based on this, the aforementioned patient state window can block part of the patient data when it is displayed; or it can also completely coexist on the display screen with the originally presented patient data. This can depend on whether the patient state window is permanently displayed or is displayed in a pop-up way, and can also depend on the size of the display screen, the number and content of the parameters originally displayed, etc. An exemplary description is given below in conjunction with FIG. 8.

Figure 8:
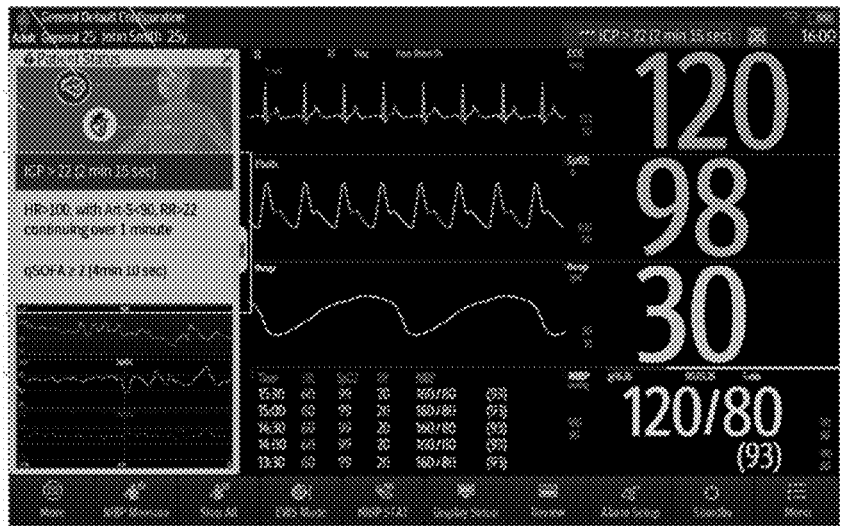
FIG. 8 is a diagram of an example of a display interface of a medical device according to an embodiment of this disclosure.

FIG. 8 is a diagram of an example of a display interface of a medical device according to an embodiment of this disclosure. As shown in FIG. 8, in addition to the patient state window mentioned above, the display interface also includes other display areas that display waveform data, numerical data, alarm information (ICP>22 in the upper right corner), etc. In such display interface, the patient state window may be permanently displayed on the display, such as permanently displayed at a fixed location of the interface (e.g., the location shown in FIG. 8). Alternatively, the patient state window may be automatically displayed on the display 130 (e.g., in a pop-up manner) when the patient state analysis result indicate that there is an abnormality in the patient. Or, when a designated icon on the display interface is triggered by the user, and the patient state window is displayed in a pop-up window.

Wherein, the designated icon can always exist, or appear, when the patient state is abnormal. For example, the designated icon can be permanently displayed at a fixed position on the interface of the display, and when the patient state indicates that the patient has an abnormality, the display mode of the designated icon can change (such as flashing, becoming larger, highlighting color, etc.), so as to prompt the user to trigger that designated icon to open the patient state window. Alternatively, when the patient state indicates an abnormality exists in the patient, the designated icon automatically appears on the display interface, so as to prompt the user to trigger the designated icon to open the patient state window.

In addition, whether it is a long-term display, an abnormal pop-up display, or a pop-up window display after triggering the designated icon, in the embodiment of this disclosure, the position of the patient state window on the display interface is capable of being set by the user. For example, the user can set the position of the patient state window on the interface in advance, or change the position of the patient state window at any time (such as by dragging) after the patient state window is displayed.

Based on the different display methods of the patient state window described above, other content may be displayed differently. In one example, the processor 120 is also configured to display other content different from the patient state window on the display 130. When the patient state window 131 is permanently displayed on the display 130, the patient state window 131 and other content are independently and completely displayed in different areas of the display 130. When the patient state window 131 is automatically displayed under a condition that the patient state indicates an abnormality exists in the patient, or when the patient state window 131 is popped up under a condition that a designated icon on the interface of the display 130 is triggered by the user, the patient state window 131 blocks at least a portion of the other content, or the layout and/or size of the other content is adaptively adjusted to be completely displayed on the display 130.

In an embodiment of this disclosure, the monitoring data acquired by the processor 120 may include real-time monitoring data which is currently monitored. The processor 120 may also be configured to generate real-time alarm information based on the real-time monitoring data, and display the real-time alarm information on the display 130. In different area on the same screen of the display, the real-time alarm information, the patient state, and the comparison result of at least one vital sign parameter with the preset alarm condition, which parameter is associated with the patient state, are displayed. Wherein patient state is presented on a human body diagram, and the comparison result is presented via text or graph. That is, the area displaying the real-time alarm information may be independent of the patient state window 131. In this embodiment, the real-time alarm information and the patient state window are displayed independently of each other, so that the medical staff can understand the patient state and simultaneously view the real-time alarm information. The following description continues with reference to FIG. 8.

Continuing to refer to FIG. 8, it can be noticed that the alarm information in an alarm area displayed in an upper right corner of FIG. 8 overlaps with the information of vital sign parameter displayed in the unit for details of a patient state of the patient state window. This is because the alarm area displayed in the upper right corner usually scrolls to display various alarm information, including physiological alarm information and technical alarm information. They are usually generated based on the real-time monitoring data, while the alarm information of the vital sign parameter displayed in the unit for details of a patient state is just the alarm information of the vital sign parameter, which parameter is associated with the current patient state (the patient state presented in the unit for a human body diagram). Therefore, under normal circumstances, the alarm area and the patient state window are independent of each other, and the amount of alarm information in the patient state window is usually less than that of the alarm information in the alarm area. From the perspective of workflow, the alarm information in the alarm area may generally appear first, and the alarm information in the patient state window only appears after the appearance of the alarm information in the alarm area, when the patient state is abnormal.

The medical device 100 according to one embodiment of this disclosure is exemplarily illustrated above. Based on the above description, the medical device 100 according to the embodiment of this disclosure analyses patient data to obtain a patient state analysis result, and graphically presents the patient state and detailly presents the parameter to medical staff in detail, so that medical staff can intuitively and clearly know the patient state, making it easier for medical staff to quickly take treatment measure according to the patient state.

Figure 9:
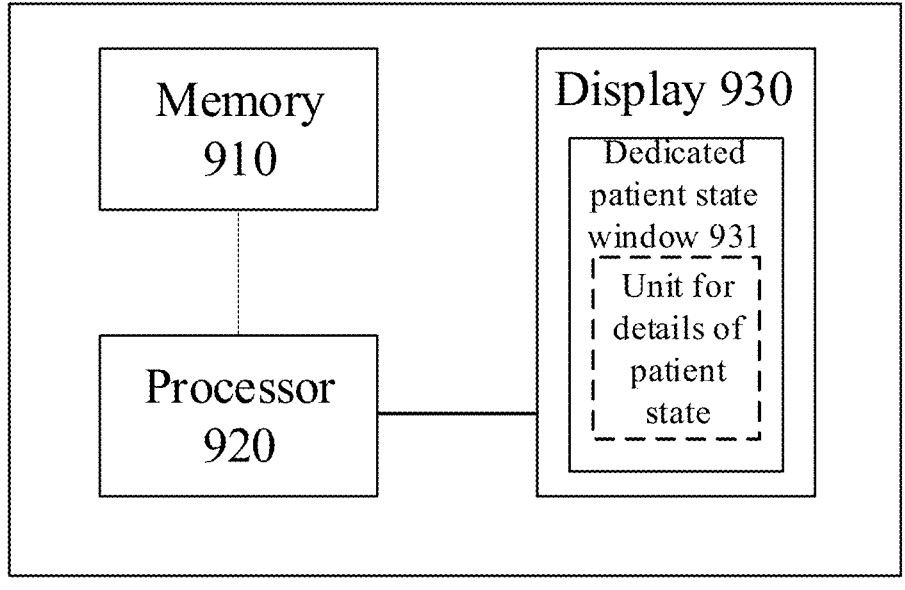
FIG. 9 is a block diagram of a medical device according to another embodiment of this disclosure.

The following describes a medical device according to another embodiment of this disclosure with reference to FIG. 9. FIG. 9 is a block diagram of a medical device according to another embodiment of this disclosure. As shown in FIG. 9, the medical device 900 may include a memory 910, a processor 920, and a display 930. Wherein the memory 910 is configured to store an executable program; the processor 920 is configured to execute the executable program, so as to enable the processor 920 to implement following operations: acquiring patient data which includes monitoring data of a patient, and analysing the patient data to obtain a state analysis result of the patient, wherein the monitoring data includes data of at least two vital sign parameters of the patient; presenting, in a patient state window 931 on the display 930, the state analysis result, wherein the patient state window 931 includes a unit for details of a patient state, wherein the state analysis result is presented by the unit for details of a patient state and includes warning information for the patient state and information of a vital sign parameter, which parameter is associated with the patient state, wherein the information of the vital sign parameter includes two pieces of information which correspond to at least one vital sign parameter, and/or two pieces of information which respectively correspond to the at least two vital sign parameters.

The medical device 900 according to the embodiment of this disclosure is generally similar to the medical device 100 described above. Those skilled in the art can understand that the components and operations of the medical device 900 based on the above description. For the sake of simplicity, same portions in the medical device 900 and the medical device 100 are not described in detail here, and just different portions in the medical device 900 and the medical device 100 are described. Compared with the medical device 100 described above, the medical device 900 according to the embodiment of this disclosure is different in that the patient state window displayed by the medical device 900 may not include the unit for a human body diagram, and the unit for details of a patient state not only displays the information of the vital sign parameter, which parameter is associated with the patient state, but also presents warning information for the patient state (such as "possible shock" mentioned above). Therefore, the medical device 900 according to the embodiment of this disclosure can analyse the patient data to obtain a patient state analysis result, and use the patient state window to present relevant vital sign parameter, which reflects the patient state, and the state warning to medical staff, so that medical staff can more accurately know the patient state and future risk, so that medical staff can quickly take treatment measure according to the patient state. Compared with the medical device 100, it only lacks the graphical display of the unit for a human body diagram, and the intuitiveness is slightly reduced.

Information display methods 1000, 1100 and 1200 for a medical device provided according to another aspect of this disclosure are described below in conjunction with FIGS. 10, 11 and 12. Methods 1000 and 1200 can be implemented by the medical device 100 described above, and the method 1100 can implemented by medical device 900. For the sake of brevity, only main steps of the methods 1000, 1100 and

1200 are described here, and their specific details are no longer described. For more details, please refer to the previous description.

As shown in FIG. 10, the information display method 1000 for a medical device may include the following steps.

In step S1010, patient data, which includes monitoring data of a patient, is acquired, and the patient data is analysed to obtain a state analysis result of the patient. Wherein the monitoring data includes data of at least two vital sign parameters of the patient.

In step S1020, the state analysis result is presented in a patient state window on the display; wherein the patient state window includes a unit for a human body diagram and a unit for details of a patient state. Wherein the unit for a human body diagram is configured to present a patient state which is associated with the state analysis result; wherein the patient state includes one or more of an overall state of the patient, a physiological system state, an organ state, a physiological part state, and a tissue state. The unit for details of a patient state is configured to present information of a vital sign parameter, which parameter is associated with the patient state, wherein the information of the vital sign parameter includes two pieces of information which correspond to at least one vital sign parameter, and/or two pieces of information which respectively correspond to the at least two vital sign parameters.

According to the information display method 1000 for a medical device according to the embodiment of this disclosure, patient data is analysed to obtain a patient state analysis result, and the patient state is graphically presented to the medical staff, and the parameters are detailly presented to the medical staff, so that the medical staff can intuitively and clearly know the patient state, making it easier for medical staff to quickly take treatment measure according to the patient state.

As shown in FIG. 11, the information display method 1100 for a medical device includes following steps.

In step S1110, patient data, which includes monitoring data of a patient, is acquired, and the patient data is analysed to obtain a state analysis result of the patient. Wherein the monitoring data includes data of at least two vital sign parameters of the patient.

In step S1120, the state analysis result is presented in a patient state window on the display; wherein the patient state window includes a unit for details of a patient state; wherein the unit for details of a patient state is configured to present the state analysis result, which includes warning information for the patient state and information of a vital sign parameter, which parameter is associated with the patient state, wherein the information of the vital sign parameter includes two pieces of information which correspond to at least one vital sign parameter, and/or two pieces of information which respectively correspond to the at least two vital sign parameters.

According to the information display method 1100 for a medical device according to the embodiment of this disclosure, patient data is analysed to obtain a patient state analysis result, and relevant vital sign parameter and warning information, which reflect a patient state, are presented to the medical staff, so that the medical staff can know the patient state and future risk more accurately, making it easier for medical staff to quickly take treatment measure according to the patient state.

As shown in FIG. 12, a display method 1200 for an interface of a monitoring device, includes following steps.

In step S1210, monitoring data of one or more vital sign parameters are displayed in real time in a first area of the interface. Wherein the first area includes at least one of a parameter waveform area, a parameter value area, a real-time alarm display area, and a patient information area, wherein data in the parameter waveform area and the parameter value area change in real time, and the monitoring data of one or more vital sign parameters are obtained from patient data of a patient.

In step S1220, a patient state is presented on a human body diagram in a second area of the interface, and a comparison result of the at least one vital sign parameter with a preset alarm condition, which parameter is associated with the patient state, is also presented via text or graph in the second area of the interface. Wherein the patient state includes one or more of an overall state of the patient, a physiological system state, an organ state, a physiological part state, and a tissue state.

In an embodiment of this disclosure, the comparison result includes an alarm which is generated when at least one vital sign parameter, which is associated with the patient state, satisfies a preset alarm condition, and a duration of the alarm.

In an embodiment of this disclosure, the comparison result is displayed on the interface, when the duration of the alarm exceeds a preset time period.

In an embodiment of this disclosure, the method 1200 further includes presenting the patient state by marking the human body diagram; wherein when the patient state includes the overall state of the patient, marking and displaying an entirety of the human body diagram; when the patient state includes one or more of a physiological system state, an organ state, a physiological part state, and a tissue state, marking and displaying one or more of physiological system, organ, physiological part and tissue, which corresponds/correspond to the patient state.

In an embodiment of this disclosure, the method 1200 further includes marking the human body diagram via at least one of graph information, symbol information, color information, and text information, which is on or adjacent to the human body diagram, so as to present the patient state.

In an embodiment of this disclosure, presenting the patient state of the patient, specifically includes presenting one or more of: whether one or more of the overall state of the patient, physiological system state, organ state, physiological part state and tissue state is/are abnormal or not; an abnormality level; a criticality level; and a nursing level.

In an embodiment of this disclosure, the preset alarm condition includes a preset alarm condition for exceeding a limit or a preset alarm condition for an abnormal event; wherein presenting, via text on the display, the comparison result of the at least one vital sign parameter with the preset alarm condition, which parameter is associated with the patient state, includes combining an alarm for exceeding a limit of and/or an alarm for an abnormal event of the at least one vital sign parameter, which parameter is associated with the patient state, with duration(s) of the alarm for exceeding a limit and/or the alarm for an abnormal event; and presenting the alarm for exceeding a limit and/or the alarm for an abnormal event, and the duration(s) of the alarm for exceeding a limit and/or the alarm for an abnormal event.

In an embodiment of this disclosure, the patient data includes monitoring data of a first vital sign parameter and monitoring data of a second vital sign parameter, wherein the preset alarm condition requires to simultaneously satisfy conditions for occurrence of a first alarm for exceeding a limit and/or a first alarm for an abnormal event, and for occurrence of a second alarm for exceeding a limit and/or a second alarm for an abnormal event; wherein presenting, via text, the comparison result of the at least one vital sign parameter with the preset alarm condition, which parameter is associated with the patient state, includes combing and presenting followings: the first alarm for exceeding a limit and/or the first alarm for an abnormal event of the first vital sign parameter, which parameter is associated with the patient state; and the second alarm for exceeding a limit and/or the second alarm for an abnormal event of the second vital sign parameter, which parameter is associated with the patient state; wherein the first alarm for exceeding a limit and/or the first alarm for an abnormal event, and the second alarm for exceeding a limit and/or the second alarm for an abnormal event, simultaneously occur.

In an embodiment of this disclosure, presenting, via text, the comparison result of the at least one vital sign parameter with the preset alarm condition, which parameter is associated with the patient state, further includes combing and presenting followings: the first alarm for exceeding a limit and/or the first alarm for an abnormal event of the first vital sign parameter, which parameter is associated with the patient state; the second alarm for exceeding a limit and/or the second alarm for an abnormal event of the second vital sign parameter, which parameter is associated with the patient state; and a duration in which: the first alarm for exceeding a limit and/or the first alarm for an abnormal event, and the second alarm for exceeding a limit and/or the second alarm for an abnormal event, simultaneously occur.

In an embodiment of this disclosure, the graph includes a curve graph, a histogram, a bar graph, a box graph, a scatter graph, a broken line graph, or a combination thereof, In an embodiment of this disclosure, the method 1200 further includes presenting, on the interface, a trend graph of the at least one vital sign parameter in a preset time period, wherein the trend graph is configured to reflect an evolution of the at least one vital sign parameter in the preset time period.

In an embodiment of this disclosure, the method 1200 further includes: presenting, in a second area of the interface, at least one of patient deterioration warning information, treatment suggestion information, and personalized concern information of the patient, which is generated based on the patient state.

In an embodiment of this disclosure, the method 1200 further includes: presenting, in the second area, a patient state window, and presenting, in the patient state window, the patient state and the comparison result of the at least one vital sign parameter with the preset alarm condition, which parameter is associated with the patient state; wherein the patient state window is permanently displayed in the second area; or the patient state window is automatically displayed in the second area when the patient state indicates that an abnormality exists in the patient; or the patient state window is popped up in the second area, when a designated icon is triggered by the user.

In an embodiment of this disclosure, the designated icon is permanently displayed at a fixed position on the interface of the display, and when the patient state indicates that the patient has an abnormality, a display mode of the designated icon changes, so as to prompt the user to trigger the designated icon for opening the patient state window; or when the patient state indicates that the patient has an abnormality, the designated icon automatically appears on the display interface, so as to prompt the user to trigger the designated icon for opening the patient state window.

In an embodiment of this disclosure, the method 1200 further includes: displaying, on the interface, other content which is different from the patient state window; when the patient state window is permanently displayed in the second area, the patient state window and the other content are independently and completely displayed in different areas of the display; when the patient state window is automatically displayed under a condition that the patient state indicates an abnormality exists in the patient, or under a condition that the user triggers the designated icon on the interface of the display to pop up the patient state window, the patient state window blocks at least a portion of the other content, or a layout and/or a size of the other content are/is adaptively adjusted to be completely displayed on the display.

In an embodiment of this disclosure, the method 1200 also includes: displaying in different areas of a same screen of the interface, real-time alarm information and the patient state window; wherein the monitoring data includes real-time monitoring data, which is currently monitored, and the real-time alarm information is generated based on the real-time monitoring data.

Based on the above description, the display method 1200 for an interface of a monitoring device not only presents the monitoring data of the vital sign parameter of the patient, but also graphically presents the patient state and detailly presents the parameter to the medical staff, so that medical staff can intuitively and clearly know the patient state, making it easier for medical staff to quickly take treatment measure according to the patient state.

Although the exemplary embodiments are described here with reference to the accompanying drawings, it should be understood that the aforementioned exemplary embodiments are only illustrative and are not intended to limit the scope of this disclosure. Ordinary technical personnel in this field can make various changes and modifications without deviating from the scope and spirit of this disclosure. All these changes and modifications are intended to be included within the scope of this disclosure as claimed in the attached claims.

Ordinary technical personnel in this field can realize that the units and algorithm steps described in combination with this disclosure can be implemented in electronic hardware, or a combination of computer software and electronic hardware. Whether these functions are executed in hardware or software depends on the specific application and design constraints of the technical solution. Professional technicians may use different methods to implement the described functions for each specific application, but such implementation should not be considered beyond the scope of this disclosure.

In the several embodiments provided in this disclosure, it should be understood that the disclosed devices and methods can be implemented in other ways. For example, the device embodiments described above are only schematic. For example, the division of the units is only a logical functional division, and there may be other division methods in actual implementations. For example, multiple units or components can be combined or integrated into another device, or some characteristics can be ignored or not executed.

The disclosure provided here provides a large number of specific details. However, it can be understood that the embodiments of this disclosure can be practiced without these specific details. In some examples, well-known methods, structures, and techniques are not shown in detail to avoid blurring the understanding of this disclosure.

Similarly, it should be understood that in order to streamline this disclosure and assist in understanding one or more of the various aspects of this disclosure, in the description of exemplary embodiments of this disclosure, the various characteristics of this disclosure are sometimes grouped together into a single embodiment, diagram, or description thereof. However, the method of this disclosure should not be interpreted as reflecting the intention that the claimed protection of this disclosure requires more characteristics than those explicitly recorded in each claim. More precisely, as reflected in the corresponding claims, the inventive point is that the corresponding technical problem can be solved with less than all characteristics of a single disclosed embodiment. Therefore, the claims following the specific implementation method are explicitly incorporated into the specific implementation method, where each claim itself serves as a separate embodiment of this disclosure.

Ordinary technical personnel in this field can understand that, except for mutual exclusion between characteristics, any combination can be configured to combine all characteristics disclosed in this disclosure (including accompanying claims, abstract, and drawings), as well as all processes or units of any method or device so disclosed. Unless otherwise explicitly stated, each characteristic disclosed in this disclosure (including accompanying claims, abstract, and accompanying drawings) may be replaced by alternative characteristics that provide the same, equivalent, or similar purpose.

In addition, Ordinary technical personnel in this field can understand that although some embodiments described herein include certain characteristics rather than other characteristics included in other embodiments, the combination of characteristics of different embodiments means that they are within the scope of this disclosure and form different embodiments. For example, in the claims, any one of the claimed embodiments can be used in any combination.

The various component embodiments of this disclosure can be implemented in hardware, software modules running on one or more processors, or a combination thereof. Ordinary technical personnel in this field should understand that a microprocessor or digital signal processor (DSP) can be used in practice to implement some or all of the functions of some modules according to the embodiments of this disclosure. This disclosure can also be implemented as a partial or complete device program (such as a computer program and a computer program product) for executing the method described herein. The program implementing this disclosure can be stored at a computer-readable medium or can have the form of one or more signals. Such signals can be downloaded from internet websites, provided on carrier signals, or in any other form.

It should be noted that the above embodiments illustrate this disclosure rather than limit it, and Ordinary technical personnel in this field can design alternative embodiments without departing from the scope of the attached claims. In the claims, any reference symbol between parentheses should not be constructed as a restriction on the claims. This disclosure can be implemented with the help of hardware consisting of several different components and with the help of appropriately programmed computers. Among the unit claims that list several devices, several of these devices can be specifically embodied through the same hardware item. The use of words first, second, and third does not indicate any order. These words can be interpreted as names.

The above is only the specific implementation method or explanation of the specific implementation method of this disclosure. The protection scope of this disclosure is not limited to this. Any technical personnel familiar with the technical field can easily think of changes or replacements within the technical scope disclosed in this disclosure, and those changes or replacements should fall into the protection scope of this disclosure. The protection scope of this disclosure shall be based on the protection scope of the claims.

What is claimed is:

1. A medical device, comprising:
a display;
a memory configured to store an executable program; and
a processor configured to execute the executable program to implement operations comprising:
acquiring patient data of a patient, wherein the patient data at least comprises monitoring data of one or more vital sign parameters of the patient;
analyzing the patient data according to a preset rule to obtain a state analysis result comprising a patient state of the patient and a comparison result of at least one vital sign parameter with a preset alarm condition, whose parameter is associated with the patient state; wherein:
the comparison result comprises an alarm and a duration of the alarm, and the alarm is generated when the at least one vital sign parameter associated with the patient state satisfies the preset alarm condition; and
the patient state comprises one or more of an overall state, a physiological system state, an organ state, a physiological part state, and a tissue state;
presenting, on a human body diagram on the display, the patient state; and
presenting, via text or graph on the display, the comparison result of the at least one vital sign parameter with the preset alarm condition, whose parameter is associated with the patient state.

2. The medical device according to claim 1, the operations further comprising:
displaying, on the display, the comparison result when the duration of the alarm exceeds a preset time period.

3. The medical device according to claim 1, wherein:
the patient state is presented by marking the human body diagram;
wherein when the patient state comprises the overall state, an entirety of the human body diagram is marked;
when the patient state comprises one or more of the physiological system state, the organ state, the physiological part state, and the tissue state, one or more of a physiological system, an organ, a physiological part, and a tissue that correspond to the patient state, are marked; or
the human body diagram is marked via at least one of graph information, symbol information, color information, and text information, which is displayed on or adjacent to the human body diagram, so as to present the patient state; or
the patient state further comprises one or more of: whether one or more of the overall state, the physiological system state, the organ state, the physiological part state, and the tissue state is/are abnormal or not an abnormality level; a criticality level; and a nursing level.

4. The medical device according to claim 1, the preset alarm condition comprises a preset alarm condition for exceeding a limit or a preset alarm condition for an abnormal event;
wherein presenting, via the text, the comparison result of the at least one vital sign parameter with the preset alarm condition, whose parameter is associated with the patient state, further comprises:
combining and presenting (1) a first alarm for exceeding a limit and/or for an abnormal event of the at least one vital sign parameter whose parameter is associated with the patient state with (2) a duration of the alarm for exceeding the limit and/or for the abnormal event, in a combined manner.

5. The medical device according to claim 1, wherein:
the patient data comprises monitoring data of a first vital sign parameter and monitoring data of a second vital sign parameter; and
the preset alarm condition comprises simultaneously satisfying (i) a first condition for occurrence of a first alarm for exceeding a limit and/or a first alarm for an abnormal event, and (ii) a second condition for occurrence of a second alarm for exceeding a limit and/or a second alarm for an abnormal event; and
presenting, via the text, the comparison result of the at least one vital sign parameter with the preset alarm condition, whose parameter is associated with the patient state, further comprises:
(A) combining (a) an alarm for exceeding a limit and/or an alarm for an abnormal event of the at least one vital sign parameter, whose parameter is associated with the patient state, with (b) one or more durations of the alarm for exceeding a limit and/for an abnormal event; and presenting in a combined manner (c) the alarm for exceeding a limit and/for an abnormal event, and (d) the one or more durations of the alarm for exceeding a limit and/for an abnormal event; or
(B) combining (1) the first alarm for exceeding a limit and/or the first alarm for an abnormal event of the first vital sign parameter, whose parameter is associated with the patient state, with (2) the second alarm for exceeding a limit and/or the second alarm for an abnormal event of the second vital sign parameter, whose parameter is associated with the patient state; and presenting the first alarm for exceeding the limit and/or the first alarm for the abnormal event of the first vital sign parameter, and the second alarm for exceeding the limit and/or the second alarm for an abnormal event of the second vital sign parameter, in a combined manner;
wherein the first alarm for exceeding a limit or the first alarm for the abnormal event, and the second alarm for exceeding the limit or the second alarm for the abnormal event simultaneously occur.

6. The medical device according to claim 5, wherein presenting, via the text, the comparison result of the at least one vital sign parameter with the preset alarm condition, whose parameter is associated with the patient state, further comprises:
combining and presenting (i) first alarm for exceeding a limit or the first alarm for an abnormal event of the first vital sign parameter, whose parameter is associated with the patient state; (ii) the second alarm for exceeding a limit or said second alarm for an abnormal event of the second vital sign parameter, whose parameter is associated with the patient state; and (iii) a duration in which the first alarm for exceeding a limit or the first alarm for the abnormal event, and the second alarm for exceeding a limit or the second alarm for an abnormal event, simultaneously occur.

7. The medical device according to claim 1, wherein the graph comprises a curve graph, a histogram, a bar graph, a box graph, a scatter graph, a broken line graph, or a combination thereof; or
the processor is further configured to control to present, on the display, a trend graph of the at least one vital sign parameter in a preset time period, the trend graph is configured to reflect an evolution of the at least one vital sign parameter in the preset time period; or the processor is further configured to control to present, on the display, at least one of patient deterioration warning information of the patient, treatment suggestion information of the patient, and personalized concern information of the patient, which is generated based on the patient state.

8. The medical device according to claim 1, the processor is further configured to present, in a patient state window on the display, the patient state and the comparison result of the at least one vital sign parameter with the preset alarm condition, whose parameter is associated with the patient state;

wherein the patient state window comprises one or more of following characteristics:

the patient state window is permanently displayed on the display;

the patient state window is automatically displayed on the display when the patient state indicates that an abnormality exists in the patient; and the patient state window is popped up when a user triggers a designated icon on an interface of the display.

9. The medical device according to claim 8, wherein:

the designated icon is permanently displayed at a fixed position on the interface of the display; and a display mode of the designated icon changes to prompt the user to trigger the designated icon for opening the patient state window, when the patient state indicates that an abnormality exists in the patient; or the designated icon automatically appears on the interface of the display to prompt the user to trigger the designated icon for opening the patient state window, when the patient state indicates that an abnormality exists in the patient; or the processor is further configured to control to display, on the display, content which is different from the patient state window; the patient state window and the content are independently and completely displayed in different areas of the display, when the patient state window is permanently displayed on the display; or the patient state window blocks at least a portion of the content, or a layout or a size of the content are/is adaptively adjusted to be completely displayed on the display; when the patient state window is automatically displayed on the display, under a condition that the patient state indicates that the abnormality exists in the patient, or when the patient state window is popped up, under a condition that the user triggers the designated icon on the interface of the display.

10. The medical device according to claim 8, wherein the monitoring data comprises real-time monitoring data, which is currently monitored; wherein the processor is further configured to generate real-time alarm information based on the real-time monitoring data;

wherein the real-time alarm information, the patient state which is presented on the human body diagram, and the comparison result of the at least one vital sign parameter with the preset alarm condition, whose parameter is associated with the patient state, are respectively displayed in different areas of a same interface of the display; wherein the comparison result is presented via text or graph.

11. The medical device according to claim 1, wherein the patient data further comprises at least one of treatment device data, drug administration data, laboratory test data, imaging data, and diagnostic data; or

the monitoring data comprises real-time monitoring data, which is currently monitored;

wherein the processor is further configured to generate real-time alarm information based on the real-time monitoring data, and to display, on the display, the real-time alarm information; wherein an area of the display, which displays the real-time alarm information, is independent of a patient state window.

12. A medical device, comprising:

a display;

a memory configured to store an executable program; and a processor configured to execute the executable program to implement operations comprising:

acquiring patient data comprising monitoring data of a patient;

analyzing the patient data to obtain a state analysis result of the patient, the monitoring data comprises data of at least two vital sign parameters of the patient; and presenting, in a patient state window on the display, the state analysis result;

wherein the patient state window comprises a unit for presenting details of a patient state, the state analysis result is presented by the unit and comprises (i) warning information for the patient state and (ii) information of a vital sign parameter whose parameter is associated with the patient state, and wherein the information of the vital sign parameter comprises (a) two pieces of information corresponding to at least one vital sign parameter, or (b) two pieces of information that respectively correspond to the at least two vital sign parameters;

wherein the information of the vital sign parameter whose information is presented by the unit for details of a patient comprises:

an alarm that corresponds to the at least one vital sign parameter, and time information which is associated with the alarm; the alarm and the time information are presented in combination in a group and jointly reflect one or more of an overall state, a same physiological system state, a same organ state, a same physiological part state and a same tissue state of the patient; and/or two alarms that respectively correspond to the at least two vital sign parameters, wherein the two alarms comprise (i) a first alarm for exceeding a limit and/or for an abnormal event of a first vital sign parameter whose parameter is associated with the patient state and (ii) a second alarm for exceeding a limit and/or for an abnormal event of a second vital sign parameter whose parameter is associated with the patient state, the first alarm for exceeding the limit and/or for the abnormal event of the first vital sign parameter and the second alarm for exceeding the limit and/or the second alarm for the abnormal event of the second vital sign parameter simultaneously occur, and the first alarm and the second alarm are presented in combination in a group and jointly reflect one or more of an overall state, a same physiological system state, a same organ state, a same physiological part state, and a same tissue state of the patient.

13. A display method for an interface of a monitoring device, comprising:

presenting, in real time in a first area of the interface, monitoring data of one or more vital sign parameters, wherein:

the first area comprises at least one of a parameter waveform area, a parameter value area, a real-time alarm display area, and a patient information area;

monitoring data in the parameter waveform area and the parameter value area change in real time; and the monitoring data of one or more vital sign parameters are obtained from patient data of a patient; and presenting, on a human body diagram in a second area of the interface, a patient state of the patient; and presenting, via text or graph in the second area of the interface, a comparison result of at least one vital sign parameter with a preset alarm condition, whose parameter is associated with the patient state;

wherein:

the comparison result comprises an alarm and a duration of the alarm, and the alarm is generated when the at least one vital sign parameter associated with the patient state satisfies the preset alarm condition; and the patient state comprises one or more of: an overall state, a physiological system state, an organ state, a physiological part state, and a tissue state.

14. The display method according to claim 13, wherein; the comparison result comprises an alarm and a duration of the alarm;

the alarm is generated when the at least one vital sign parameter associated with the patient state satisfies the preset alarm condition; and the comparison result is displayed on the interface when the duration of the alarm exceeds a preset time period.

15. The display method according to claim 13, wherein:

the preset alarm condition comprises a preset alarm condition for exceeding a limit or a preset alarm condition for an abnormal event;

presenting, via the text, the comparison result of the at least one vital sign parameter with the preset alarm condition, whose parameter is associated with the patient state, comprises:

combining (i) an alarm for exceeding a limit of and/or for an abnormal event of the at least one vital sign parameter, whose parameter is associated with the patient state with (ii) one or more durations of the alarm for exceeding the limit of and/or for the abnormal event; and presenting the (a) alarm for exceeding the limit of and/or for the abnormal event and (b) the one or more durations of the alarm for exceeding the limit of and/or for the abnormal event, in a combined manner.

16. The display method according to claim 13, wherein;

the patient data comprises monitoring data of a first vital sign parameter and monitoring data of a second vital sign parameter; and the preset alarm condition comprises simultaneously satisfying (i) a first condition for occurrence of a first alarm for exceeding a limit and/or for an abnormal event of the first vital sign parameter whose parameter is associated with the patient state, and (ii) a second condition for occurrence of a second alarm for exceeding a limit and/or for an abnormal event of the second vital sign parameter whose parameter is associated with the patient state;

wherein presenting, via the text, the comparison result of the at least one vital sign parameter with the preset alarm condition whose parameter is associated with the patient state, comprises:

combining and presenting (i) the first alarm for exceeding a limit of and/or for the abnormal event of the first vital sign parameter whose parameter is associated with the patient state and (ii) the second alarm for exceeding a limit of and/or for the abnormal event of the second vital sign parameter whose parameter is associated with the patient state, in a combined manner;

wherein (a) the first alarm for exceeding limit and/or for the abnormal event, and (b) the second alarm for exceeding the limit and/or for the abnormal event simultaneously occur.

17. The display method according to claim 16, wherein presenting, via text, the comparison result of the at least one vital sign parameter with the preset alarm condition, whose parameter is associated with the patient state, further comprises:

combining and presenting (i) the first alarm for exceeding the limit of and/or for the abnormal event of the first vital sign parameter, whose parameter is associated with the patient state; and (ii) the second alarm for exceeding the limit of and/or for the abnormal event of the second vital sign parameter, whose parameter is associated with the patient state; and (iii) a duration in which the first alarm for exceeding the limit and/or for the abnormal event, and the second alarm for exceeding the limit and/or for the abnormal event, simultaneously occur, in a combined manner.

18. The display method according to claim 13, further comprising:

presenting, in the second area of the interface, a patient state window; and presenting, in the patient state window, the patient state and the comparison result of the at least one vital sign parameter with the preset alarm condition whose parameter is associated with the patient state; wherein:

the patient state window is permanently displayed in the second area;

the patient state window is automatically displayed in the second area, when the patient state indicates that an abnormality exists in the patient; and the patient state window is popped up in the second area, when a user triggers a designated icon.

19. The display method according to claim 18, wherein:

the designated icon is permanently displayed at a fixed position on the interface of the display; and a display mode of the designated icon changes to prompt the user to trigger the designated icon for opening the patient state window, when the patient state indicates that an abnormality exists in the patient; or the designated icon automatically appears on the interface of the display to prompt the user to trigger the designated icon for opening the patient state window, when the patient state indicates that an abnormality exists in the patient; or the display method further comprises displaying, on the interface, content which is different from the patient state window; the patient state window and the content are independently and completely displayed in different areas of the interface, when the patient state window is permanently displayed in the second area; or the patient state window blocks at least a portion of the content, or a layout or a size of the content is adaptively adjusted to be completely displayed on the interface; when the patient state window is automatically displayed in the second area, under a condition that the patient state indicates that the abnormality exists in the patient, or when the patient state window is popped up in the second area, under a condition that the user triggers the designated icon.

* * * * *

26